US011602333B2

(12) United States Patent
Ota et al.

(10) Patent No.: US 11,602,333 B2
(45) Date of Patent: Mar. 14, 2023

(54) ULTRASOUND DIAGNOSTIC APPARATUS

(71) Applicant: KONICA MINOLTA, INC., Tokyo (JP)

(72) Inventors: Kazushi Ota, Tokyo (JP); Akihiro Kawabata, Tokyo (JP); Masumi Osugi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/904,631

(22) Filed: Jun. 18, 2020

(65) Prior Publication Data

US 2020/0405270 A1 Dec. 31, 2020

(30) Foreign Application Priority Data

Jun. 25, 2019 (JP) .............................. JP2019-117550

(51) Int. Cl.
*A61B 8/00* (2006.01)
*G01S 15/89* (2006.01)
(Continued)

(52) U.S. Cl.
CPC ................. *A61B 8/54* (2013.01); *A61B 8/06* (2013.01); *A61B 8/14* (2013.01); *A61B 8/488* (2013.01); *G01S 15/8993* (2013.01)

(58) Field of Classification Search
CPC .... A61B 8/54; A61B 8/06; A61B 8/14; A61B 8/488; A61B 8/4405; A61B 8/5207;
(Continued)

(56) References Cited

U.S. PATENT DOCUMENTS 5,513,640 A * 5/1996 Yamazaki .......... G01N 29/0609
600/455
2013/0281855 A1 10/2013 Baba et al.
2014/0276072 A1* 9/2014 Martins ................. A61B 8/488
600/454

FOREIGN PATENT DOCUMENTS

JP 2002301077 A 10/2002
JP 2004195018 A 7/2004
(Continued)

OTHER PUBLICATIONS

Japanese Office Action (and English language translation thereof) dated Dec. 20, 2022, issued in counterpart Japanese Application No. 2019-117550.

*Primary Examiner* — Bo Joseph Peng
(74) *Attorney, Agent, or Firm* — Holtz, Holtz & Volek PC

(57) ABSTRACT

An ultrasound diagnostic apparatus includes: a transmitter; a receiver; a Doppler processor that detects a Doppler shift frequency resulting from a blood flow in a subject, based on a reception signal corresponding to a reflected wave from a sample gate position in the subject; and a velocity scale adjuster that adjusts a velocity scale determining a pulse repetition frequency, based on a Doppler waveform corresponding to the Doppler shift frequency during an observation target period. In a case where a recommendation value of the velocity scale calculated based on the Doppler waveform is larger than a critical value of the velocity scale at which a measurement state calculated based on the sample gate position transitions from a non-high-pulse-repetition-frequency state to a high-pulse-repetition-frequency state, the velocity scale adjuster sets the critical value as the velocity scale to be used in measurement.

5 Claims, 12 Drawing Sheets

(51) Int. Cl.
*A61B 8/14* (2006.01)
*A61B 8/08* (2006.01)
*A61B 8/06* (2006.01)

(58) Field of Classification Search
CPC . A61B 8/5223; G01S 15/8993; G01S 7/5205; G01S 7/52066
See application file for complete search history.

(56) References Cited

FOREIGN PATENT DOCUMENTS

| | | | |
|---|---|---|---|
| JP | 2007202617 | A | 8/2007 |
| JP | 2010088943 | A | 4/2010 |
| JP | 2010136808 | A | 6/2010 |
| JP | 2012139489 | A | 7/2012 |

* cited by examiner

| DIAGNOSIS AREA | VELOCITY SCALE REFERENCE FACTOR |
|---|---|
| HEART | 0.95 |
| OTHER THAN HEART (e.g. BLOOD VESSEL) | 0.70 |

ULTRASOUND DIAGNOSTIC APPARATUS

CROSS REFERENCE TO RELATED APPLICATIONS

The entire disclosure of Japanese Patent Application No. 2019-117550 filed on Jun. 25, 2019 is incorporated herein by reference in its entirety.

BACKGROUND

Technological Field

The present disclosure relates to an ultrasound diagnostic apparatus.

Description of Related Art

An ultrasound diagnostic apparatus that employs a pulse-Doppler system to measure the blood flow velocity and so on of a subject is widely used. This type of ultrasound diagnostic apparatus transmits a pulsed ultrasound beam toward a subject at a predetermined pulse repetition frequency (PRF). This type of ultrasound diagnostic apparatus sets a sample gate position as a measurement target region and displays a Doppler waveform on the basis of the Doppler shift frequency of an ultrasonic echo that is received at a timing corresponding to the sample gate position.

FIG. 1 is a diagram illustrating an example monitor screen displayed when a blood flow is measured. The left part of FIG. 1 is a tomographic image (in this example, an image of a heart region), and the right part is an image of a Doppler waveform. The mark displayed on the tomographic image (the region outlined by the dashed line) indicates a sample gate position set as a target region that is measured with a pulse-Doppler system.

The Doppler waveform is displayed as, for example, spectral display as illustrated in FIG. 1 where the time is represented by the horizontal axis, the Doppler shift frequency (that is, the blood flow velocity) is represented by the vertical axis, and the power (intensity) of each frequency component is represented as brightness (gradation). From the Doppler waveform, for example, the maxim and average blood flow velocities, the waveform peak PS (Peak of Systolic) during systole and the waveform peak ED (End of Diastolic) during diastole per cardiac cycle (per cardiac beat), and so on are obtained.

The blood flow velocity of a subject differs depending on the diagnosed area or the condition of the living body. Depending on the setting of a velocity scale that determines the displayable range of blood flow velocity, the Doppler waveform may fold over and be displayed or the Doppler waveform may look very small relative to the proportion of the display screen. Note that the "velocity scale" determines the PRF at which the ultrasound beam is transmitted, and determines the maximum value of the measurable blood flow velocity.

Against such a background, as this type of ultrasound diagnostic apparatus, an apparatus having a function of automatically adjusting the velocity scale so as to optimize the magnitude of the Doppler waveform (that is, resolution and visibility) is currently available (for example, see Japanese Patent Application Laid-Open No. 2010-088943).

FIGS. 2A and 2B are diagrams for describing the function of automatically adjusting the velocity scale of the ultrasound diagnostic apparatus according to the related art. FIG. 2A illustrates a Doppler waveform before automatic adjustment of the velocity scale, and FIG. 2B illustrates the Doppler waveform after automatic adjustment of the velocity scale. In FIGS. 2A and 2B, "0" represents the position (baseline) at which the Doppler shift frequency (that is, the blood flow velocity) is zero, Vs represents the velocity scale, T represents the observation target period, and Vm represents the maximum value (peak-to-peak) of the Doppler shift frequency (that is, the blood flow velocity) during the observation target period.

In this type of ultrasound diagnostic apparatus, for example, maximum value Vm of the Doppler shift frequency during observation target period T is calculated with reference to the Doppler waveform in the immediately preceding observation target period T, and the optimum value of velocity scale Vs as expressed by expression (1) below is calculated on the basis of maximum value Vm and velocity scale reference factor α. Then, the calculated optimum value of velocity scale Vs is set as the setting of the velocity scale. Note that "velocity scale reference factor α" is a factor that determines the magnitude of the velocity scale relative to maximum value Vm of the Doppler shift frequency during observation target period T (reciprocal relationship), and is set to, for example, about 0.7.

$$Vs = Vm \div \alpha \qquad \text{expression (1)}$$

(Here, Vs represents the optimum value of the velocity scale, α represents the velocity scale reference factor, and Vm represents the maximum value of the Doppler shift frequency during observation target period T.)

That is, the automatic adjustment function for the velocity scale makes an automatic adjustment so as to increase the velocity scale when the measurement target blood flow velocity is high and to decrease the velocity scale when the measurement target blood flow velocity is low. To calculate the optimum value of velocity scale Vs, the average blood flow velocity during the observation target period may be used.

In this type of ultrasound diagnostic apparatus, the measurable Doppler shift frequency (that is, the measurable blood flow velocity) is limited in accordance with the PRF of the ultrasound beam equivalent to the sampling frequency. Specifically, as the PRF is increased, the upper limit of the measurable blood flow velocity increases, and as the PRF is decreased, the upper limit of the measurable blood flow velocity decreases. When the actual blood flow velocity exceeds the range of measurable blood flow velocity determined by the PRF, an aliasing phenomenon (folding) occurs.

In the related art, in this type of ultrasound diagnostic apparatus, a high pulse repetition frequency (HPRF) measurement method for increasing the PRF may be used to increase the upper limit of the measurable blood flow velocity.

FIG. 3 is a diagram illustrating a measurement state in the HPRF measurement method (hereinafter referred to as "HPRF state"). In FIG. 3, R represents the entire region of a tomographic image, R1 represents the sample gate, and R2 represents a sub-gate.

In the HPRF measurement method, the sample gate position is set to a position deeper than a reference depth to which the ultrasound beam makes a round trip in one period of the pulse repetition time (the reciprocal of the repetition frequency). Therefore, before the previously transmitted ultrasound beam reflected at the sample gate position is received as the observation target reflected wave, the next ultrasound beam is transmitted.

In the HPRF state, a region called sub-gate R2 is present at a position at which the time taken by the ultrasound transmitted from an ultrasonic probe to return to the ultrasonic probe after reflection in the subject matches the time obtained by subtracting the time for one period of the pulse repetition time from the time taken to make a round trip to the sample gate (which is the time taken by the ultrasound to make a round trip between the ultrasonic probe and sample gate R1). In other words, sub-gate R2 is present at a position at which the depth from the ultrasonic probe is a depth equivalent to the distance from reference depth D0 to sample gate R1, reference depth D0 being a depth to which the ultrasound makes a round trip in the time for one period of the pulse repetition time.

At this time, in a case where tissue that reflects the ultrasound does not exist at sub-gate R2, sufficient measurement accuracy is achieved even in the HPRF state. However, in a case where tissue that reflects the ultrasound exists at sub-gate R2, unwanted ultrasound resulting from part of the succeeding ultrasound beam reflected at sub-gate R2 is received by the ultrasonic probe in the time period of the observation target ultrasound, and the unwanted ultrasound interferes with the observation target ultrasound, which leads to a problem of a decrease in measurement accuracy.

A skilled user can fully understand the principle of the HPRF measurement method and its advantages and disadvantages described above and increase the velocity scale to intentionally measure the blood flow in the HPRF state. However, an unskilled user might not grasp a phenomenon occurring in the HPRF state and may measure the blood flow in a state where measurement accuracy decreases.

Specifically, as illustrated FIGS. 2A and 2B, in the case where the velocity scale is automatically adjusted, the optimum value of the velocity scale on display is calculated regardless of the velocity scale that leads to the HPRF state. Therefore, in the ultrasound diagnostic apparatus according to the related art, when the velocity scale is automatically adjusted, the velocity scale may be set to a large value (that is, the PRF may be set to a large value), and the blood flow may be measured in a state where an unintended transition to the HPRF state occurs.

Such a situation is likely to occur in a case where, for example, the sample gate position is set to a deep position or the measurement target blood flow velocity is high. The reasons are as follows. In the case where the sample gate position is set to a deep position, the velocity scale that leads to the HPRF state inevitably decreases. In the case where the measurement target blood flow velocity is high, the velocity scale that is set by automatic adjustment increases.

SUMMARY

The present disclosure has been made in view of the above-described problems, and an object thereof is to provide an ultrasound diagnostic apparatus that can automatically adjust the velocity scale to be used in generation of the Doppler waveform while avoiding an unintended transition to the HPRF state.

To achieve at least one of the abovementioned objects, according to an aspect of the present invention, an ultrasound diagnostic apparatus reflecting one aspect of the present invention comprises:

a transmitter that repeatedly transmits an ultrasound beam from an ultrasonic probe into a subject at a predetermined pulse repetition frequency;

a receiver that receives via the ultrasonic probe a reflected wave resulting from the ultrasound beam reflected in the subject;

a Doppler processor that detects a Doppler shift frequency resulting from a blood flow or motion of tissue in the subject, based on a reception signal corresponding to the reflected wave from a sample gate position in the subject; and a velocity scale adjuster that adjusts a velocity scale determining the pulse repetition frequency, based on a Doppler waveform corresponding to the Doppler shift frequency during an observation target period, wherein in a case where a recommendation value of the velocity scale calculated based on the Doppler waveform is larger than a critical value of the velocity scale at which a measurement state calculated based on the sample gate position transitions from a non-high-pulse-repetition-frequency state to a high-pulse-repetition-frequency state, the velocity scale adjuster sets the critical value as the velocity scale to be used in measurement.

To achieve at least one of the abovementioned objects, according to another aspect of the present invention, an ultrasound diagnostic apparatus reflecting one aspect of the present invention comprises:

a transmitter that repeatedly transmits an ultrasound beam from an ultrasonic probe into a subject at a predetermined pulse repetition frequency;

a receiver that receives via the ultrasonic probe a reflected wave resulting from the ultrasound beam reflected in the subject;

a Doppler processor that detects a Doppler shift frequency resulting from a blood flow or motion of tissue in the subject, based on a reception signal corresponding to the reflected wave from a sample gate position in the subject; and a velocity scale adjuster that adjusts a velocity scale determining the pulse repetition frequency, based on a Doppler waveform corresponding to the Doppler shift frequency during an observation target period, wherein in a case where a recommendation value of the velocity scale calculated based on the Doppler waveform is larger than a critical value of the velocity scale at which a measurement state calculated based on the sample gate position transitions from a non-high-pulse-repetition-frequency state to a high-pulse-repetition-frequency state, the velocity scale adjuster lowers a transmission frequency of the ultrasound beam from an initially set frequency.

To achieve at least one of the abovementioned objects, according to another aspect of the present invention, an ultrasound diagnostic apparatus reflecting one aspect of the present invention comprises:

a transmitter that repeatedly transmits an ultrasound beam from an ultrasonic probe into a subject at a predetermined pulse repetition frequency;

a receiver that receives via the ultrasonic probe a reflected wave resulting from the ultrasound beam reflected in the subject;

a Doppler processor that detects a Doppler shift frequency resulting from a blood flow or motion of tissue in the subject, based on a reception signal corresponding to the reflected wave from a sample gate position in the subject; and a velocity scale adjuster that adjusts a velocity scale determining the pulse repetition frequency, based on a Doppler waveform corresponding to the Doppler shift frequency during an observation target period, wherein the velocity scale adjuster sets a factor that determines a magnitude of the velocity scale relative to a maximum value of the Doppler shift frequency during the observation target period, based on a diagnostic condition set by a user, and sets the velocity scale to be used in measurement, based on the factor and the Doppler waveform.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
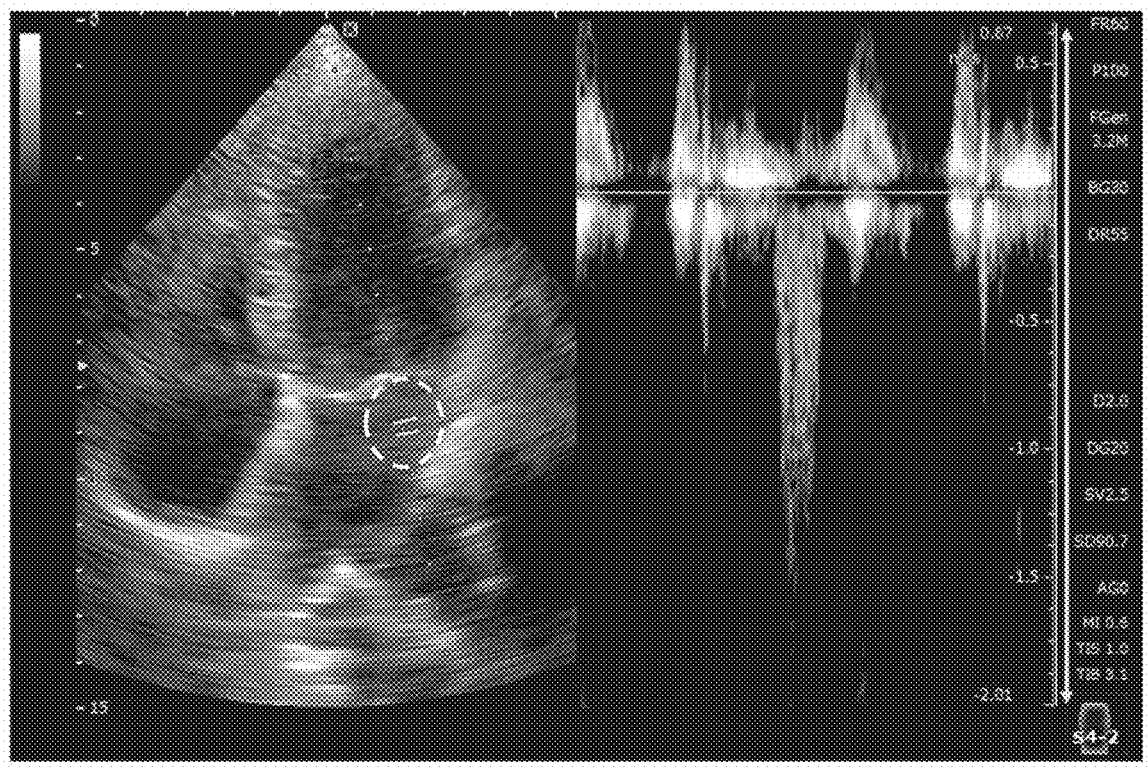
FIG. 1 is a diagram illustrating an example monitor screen displayed when a blood flow is measured.

Hereinafter, one or more embodiments of the present invention will be described with reference to the drawings. However, the scope of the invention is not limited to the disclosed embodiments.

Preferred embodiments of the present disclosure will be described in detail with reference to the attached drawings. Note that elements having substantially the same functions are assigned the same reference numerals in the description and drawings to omit duplicated descriptions thereof.

First Embodiment

Configuration of Ultrasound Diagnostic Apparatus

Figure 5:
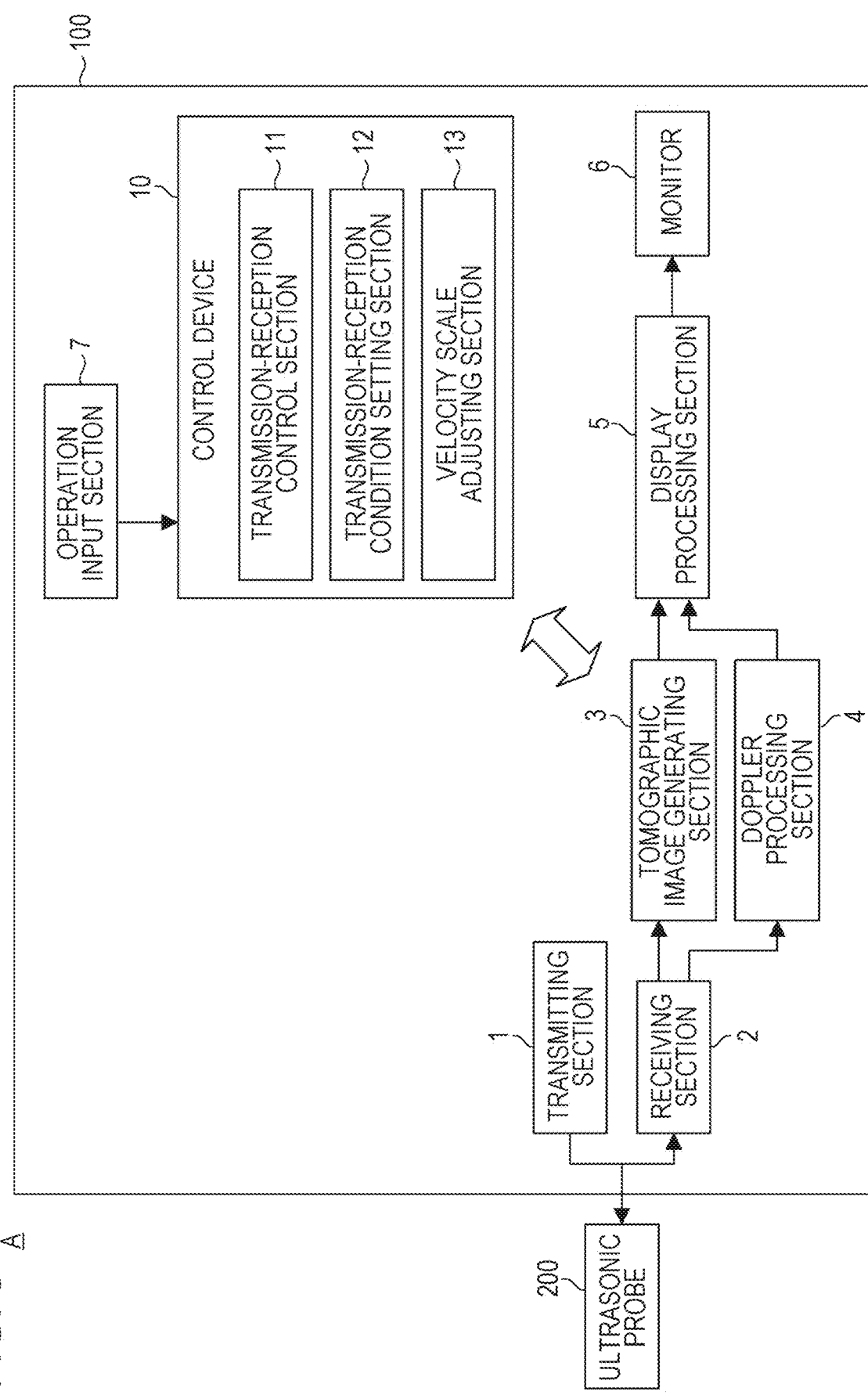
FIG. 5 is a diagram illustrating an example overall configuration of the ultrasound diagnostic apparatus according to the first embodiment.
Figure 6:
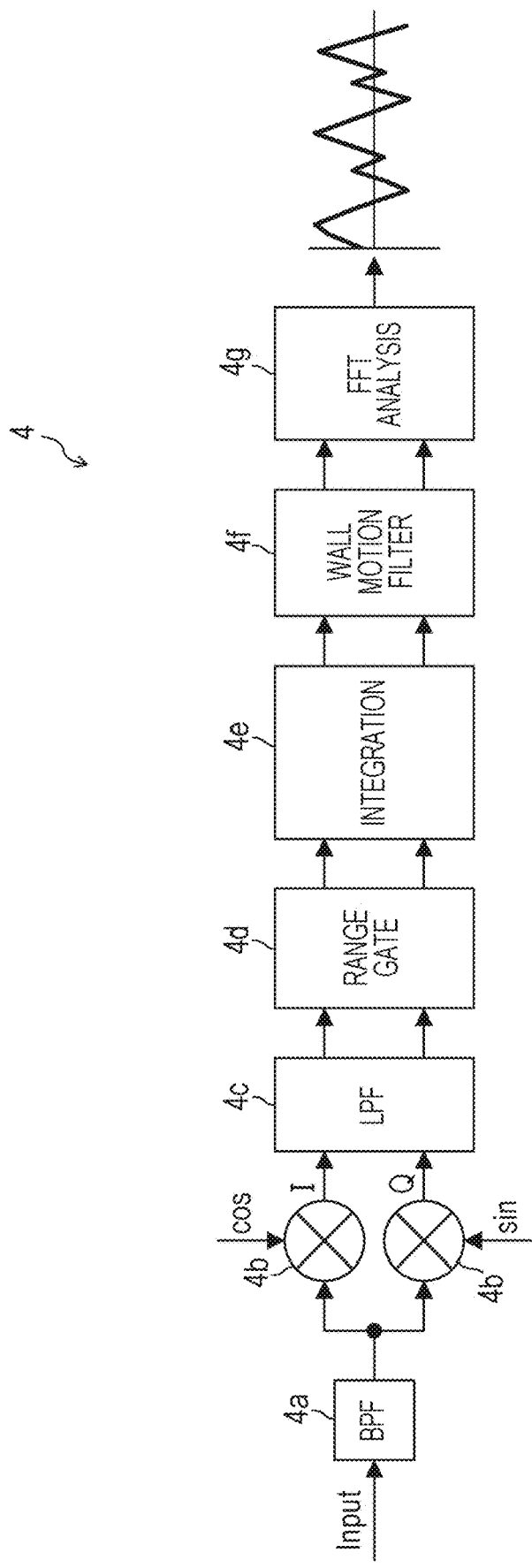
FIG. 6 is a diagram illustrating an example configuration of a Doppler processing section of the ultrasound diagnostic apparatus according to the first embodiment.

The configuration of an ultrasound diagnostic apparatus according to a first embodiment of the present invention will be described with reference to FIGS. 4, 5, and 6.

Figure 4:
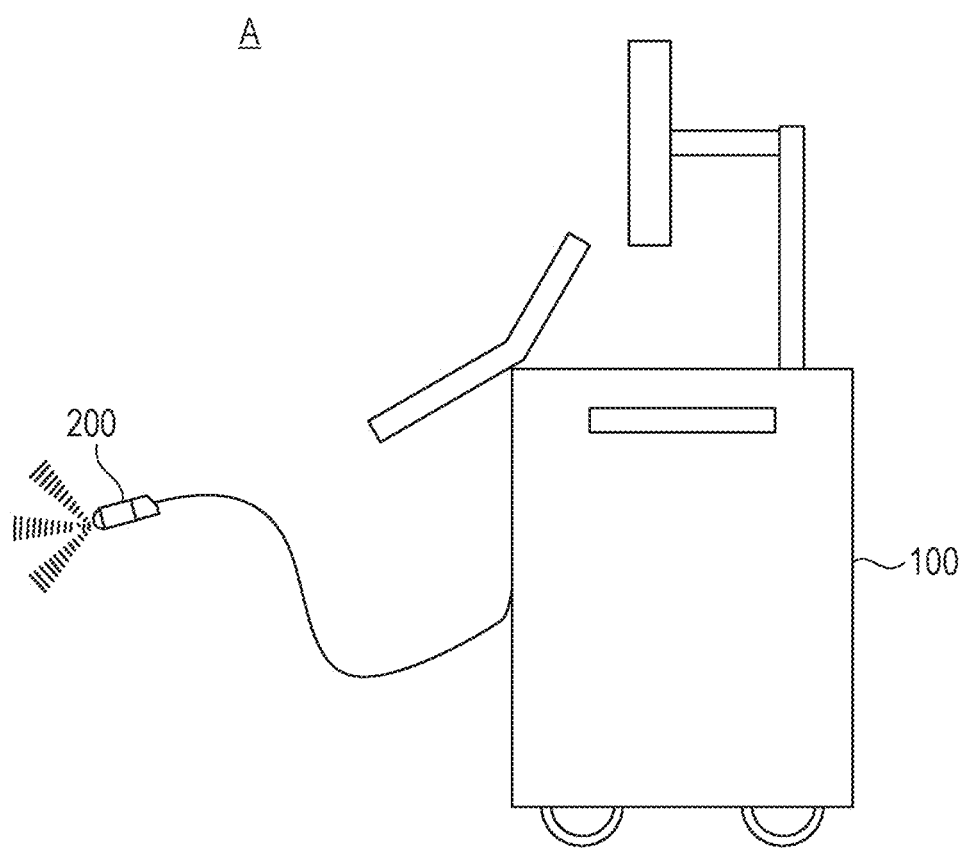
FIG. 4 is a diagram illustrating an external view of an ultrasound diagnostic apparatus according to a first embodiment.

FIG. 4 is a diagram illustrating an external view of ultrasound diagnostic apparatus A according to this embodiment. FIG. 5 is a diagram illustrating an example overall configuration of ultrasound diagnostic apparatus A according to this embodiment. FIG. 6 is a diagram illustrating an example configuration of Doppler processing section 4 of ultrasound diagnostic apparatus A according to this embodiment.

Ultrasound diagnostic apparatus A is used to visualize the shape, properties, or dynamic state of an area in a subject as an ultrasound image to make an image-based diagnosis. In this embodiment, a form is described in which ultrasound diagnostic apparatus A performs a B-mode operation and a pulse-Doppler-mode operation in a time-division manner to generate a tomographic image and a Doppler waveform.

As illustrated in FIG. 4, ultrasound diagnostic apparatus A includes ultrasound diagnostic apparatus main body 100 and ultrasonic probe 200. Ultrasound diagnostic apparatus main body 100 and ultrasonic probe 200 are connected to each other via a cable.

Ultrasonic probe 200 functions as an acoustic sensor that transmits an ultrasound beam (here, about 1 to 30 MHz) into a subject (for example, a human body), receives an ultrasonic echo resulting from part of the transmitted ultrasound beam reflected in the subject, and converts the ultrasonic echo to an electric signal.

A user brings the ultrasound-beam transmission-reception surface of ultrasonic probe 200 into contact with a subject and operates ultrasound diagnostic apparatus A to make an ultrasonic diagnosis. It is assumed here that ultrasonic probe 200 transmits the ultrasound beam from the outer surface of the subject into the subject and receives the resulting ultrasonic echo; however, ultrasonic probe 200 may be an ultrasonic probe that is inserted, for example, into the alimentary canal or blood vessel or into the coelom and used. As ultrasonic probe 200, any probe, such as a convex probe, a linear probe, a sector probe, or a 3D probe, is applicable.

Ultrasonic probe 200 includes, for example, a plurality of transducers (for example, piezoelectric elements) arranged in a matrix and a channel switching section (for example, a multiplexer) for performing switching control to turn on and off of the driving states of the plurality of transducers individually or for each block (hereinafter referred to as "channel").

Each transducer of ultrasonic probe 200 converts a voltage pulse generated by ultrasound diagnostic apparatus main body 100 (transmitting section 1) to an ultrasound beam, transmits the ultrasound beam into a subject, receives an ultrasonic echo reflected in the subject, converts the ultrasonic echo to an electric signal (hereinafter referred to as "reception signal"), and outputs the reception signal to ultrasound diagnostic apparatus main body 100 (receiving section 2).

Ultrasound diagnostic apparatus main body 100 includes transmitting section 1, receiving section 2, tomographic image generating section 3, Doppler processing section 4, display processing section 5, monitor 6, operation input section 7, and control device 10.

Transmitting section 1 is a section that transmits a voltage pulse serving as a driving signal to ultrasonic probe 200. Transmitting section 1 includes, for example, a radio-frequency pulse oscillator and a pulse setting section. Transmitting section 1 adjusts a voltage pulse generated by the radio-frequency pulse oscillator so as to have a voltage amplitude, a pulse width, and a transmission timing set by the pulse setting section, and transmits the voltage pulse to ultrasonic probe 200.

Transmitting section 1 includes the pulse setting section for each of the plurality of channels of ultrasonic probe 200 so that the voltage amplitude, the pulse width, and the transmission timing of the voltage pulse can be set for each channel. For example, transmitting section 1 sets an appropriate delay time for each of the plurality of channels to change a target depth or generate different pulse waveforms.

In the pulse-Doppler-mode operation, transmitting section 1 is controlled by control device 10 (transmission-reception control section 11) so as to repeatedly transmit an ultrasound beam into a subject from ultrasonic probe 200 at a predetermined PRF.

Receiving section 2 is a section that receives and processes a reception signal corresponding to an ultrasonic echo and generated by ultrasonic probe 200. Receiving section 2 includes a preamplifier, an analog-digital (AD) converting section, and a reception beamformer.

Receiving section 2 amplifies, for each channel, a reception signal corresponding to a weak ultrasonic echo and converts the reception signal to a digital signal by the preamplifier and the AD conversion section provided for each channel. Receiving section 2 phases and adds up the reception signals of the respective channels by the reception beamformer to thereby put the reception signals of the plurality of channels together and generate acoustic line data.

Tomographic image generating section 3 obtains a reception signal from receiving section 2 during the B-mode operation and generates a tomographic image (also referred to as "B-mode image") of the inside of the subject (see the left part of FIG. 1).

For example, when ultrasonic probe 200 transmits a pulsed ultrasound beam in the depth direction, tomographic image generating section 3 accumulates the signal intensity of an ultrasonic echo detected thereafter in a line memory continuously over time. As the ultrasound beam from ultrasonic probe 200 is scanned across the inside of the subject, tomographic image generating section 3 successively accumulates in the line memory the signal intensity of the ultrasonic echo at each scan position to generate 2D data on a per frame basis. Tomographic image generating section 3 converts the signal intensity of the ultrasonic echo detected at each position inside the subject to a brightness value to thereby generate a tomographic image.

Tomographic image generating section 3 includes, for example, an envelope detector circuit, a dynamic filter, and a logarithmic compression circuit. The envelope detector circuit performs envelope detection on the reception signal to detect the signal intensity. The logarithmic compression circuit performs logarithmic compression on the signal intensity of the reception signal detected by the envelope detector circuit. The dynamic filter is a bandpass filter having a frequency characteristic that is changed in accordance with the depth, and removes a noise component included in the reception signal.

Doppler processing section 4 obtains a reception signal from receiving section 2 during the pulse-Doppler-mode operation and detects the Doppler shift frequency of the ultrasonic echo from the sample gate position. Doppler processing section 4 generates a Doppler waveform (see the right part of FIG. 1) that represents temporal changes in the detected Doppler shift frequency.

While ultrasonic probe 200 is transmitting a pulsed ultrasound beam at regular intervals in accordance with the PRF, Doppler processing section 4 samples a reception signal corresponding to the ultrasonic echo in synchronization with the PRF. Doppler processing section 4 detects the Doppler shift frequency on the basis of the phase difference between, for example, the ultrasonic echo corresponding to the n-th ultrasound beam and the ultrasonic echo corresponding to the n+1-th ultrasound beam from the same sample gate position.

Doppler processing section 4 includes, for example, bandpass filter 4a, quadrature detector section 4b, lowpass filter 4c, range gate 4d, integrating circuit 4e, wall motion filter 4f, and fast Fourier transform (FFT) analyzing section 4g. Bandpass filter 4a removes an unwanted frequency component. Quadrature detector section 4b mixes the reception signal with a reference signal that is in phase with the transmitted ultrasound beam and with a reference signal having a phase different from the phase of the transmitted ultrasound beam by π/2 to generate quadrature detection signals. Lowpass filter 4c removes high-frequency components from the quadrature detection signals to generate the reception signal that corresponds to the Doppler shift frequency. Range gate 4d obtains only the ultrasonic echo from the sample gate position. Integrating circuit 4e integrates the reception signal obtained by range gate 4d. Wall motion filter 4f performs low-range removal to remove the clutter component (the ultrasonic echo from tissue). FFT analyzing section 4g performs a frequency analysis on the Doppler shift frequency component of the reception signal thus obtained.

Taking into consideration the crossing angle between the beam direction of the ultrasound beam and the blood flow direction at the sample gate position, Doppler processing section 4 may generate a Doppler waveform by converting the Doppler shift frequency to the blood flow velocity as expressed by expression (2) below.

$$V = c/2 \cos \theta \times Fd/F0 \qquad \text{expression (2)}$$

(Here, V represents the blood flow velocity, F0 represents the transmission frequency of the ultrasound beam, Fd represents the Doppler shift frequency, c represents the in vivo sound velocity, and θ represents the crossing angle (angle correction value)).

Display processing section 5 obtains a tomographic image output from tomographic image generating section 3 and a Doppler waveform output from Doppler processing section 4 and generates a display image to be displayed on monitor 6.

The display image generated by display processing section 5 includes an image indicating a condition for performing the pulse-Doppler mode (that is, a diagnostic condition) and an image of a message box for notifying the user of an error occurring while the pulse-Doppler mode is being performed as well as the tomographic image and the Doppler waveform.

Monitor 6 is a display that displays a display image generated by display processing section 5, and is, for example, a liquid crystal display.

Operation input section 7 is a user interface for the user to perform input operations and includes, for example, a push-button switch, a keyboard, and a mouse. Operation input section 7 converts an input operation performed by the user to an operation signal and inputs the operation signal to control device 10.

Control device 10 mutually exchanges signals with ultrasonic probe 200, transmitting section 1, receiving section 2, tomographic image generating section 3, Doppler processing section 4, display processing section 5, monitor 6, and operation input section 7 and centrally controls these sections.

Control device 10 includes transmission-reception control section 11, transmission-reception condition setting section 12, and velocity scale adjusting section 13.

Transmission-reception control section 11 controls the channel switching section (not illustrated) of ultrasonic probe 200 to selectively determine driving target channels among the plurality of channels. Transmission-reception control section 11 controls transmitting section 1 and receiving section 2 to transmit and receive ultrasound for the driving target channels.

Transmission-reception control section 11 sequentially drives in the scan direction the driving target channels among the plurality of channels during the B-mode operation (that is, in a case of generating a tomographic image) to thereby scan the inside of the subject with ultrasound by using ultrasonic probe 200.

During the pulse-Doppler-mode operation (that is, in a case of measuring the blood flow velocity), transmission-reception control section 11 selectively drives the plurality of transducers provided in ultrasonic probe 200 so that an ultrasound beam is transmitted to the sample gate position in the subject from ultrasonic probe 200 at a predetermined angle. At this time, transmission-reception control section 11 controls transmitting section 1 so that a pulsed ultrasound beam is repeatedly transmitted from ultrasonic probe 200 at a predetermined PRF, and controls receiving section 2 so as to receive an ultrasonic echo resulting from the ultrasound beam.

Transmission-reception condition setting section 12 sets a transmission condition for the ultrasound beam and a reception condition for the ultrasonic echo, the conditions determining the operation of transmission-reception control section 11. Transmission-reception condition setting section 12 determines the transmission condition and the reception condition on the basis of, for example, the type of ultrasonic probe 200 (for example, the convex type, the sector type, or the linear type), the diagnosis target area in the subject, the sex of the subject, or the age of the subject. During the pulse-Doppler-mode operation, transmission-reception condition setting section 12 determines the transmission condition and the reception condition on the basis of the sample gate position, the size of the sample gate, and the beam direction of the ultrasound beam (that is, the steering angle). As the transmission condition and the reception condition, conditions set by the user via operation input section 7 are typically used.

Velocity scale adjusting section 13 adjusts the velocity scale that determines the PRF in the pulse-Doppler-mode operation. Velocity scale adjusting section 13 is configured to be capable of automatically adjusting the velocity scale so as to, for example, optimize the magnitude of the Doppler waveform. Note that velocity scale adjusting section 13 according to this embodiment performs the adjustment process so that a transition to the HPRF state can be avoided when the pulse-Doppler mode is performed.

Velocity scale adjusting section 13 may automatically adjust the position of the baseline (that is, the position at which the blood flow velocity is zero) using a known technique simultaneously with adjustment of the velocity scale.

Configuration of Velocity Scale Adjusting Section

Figure 7:
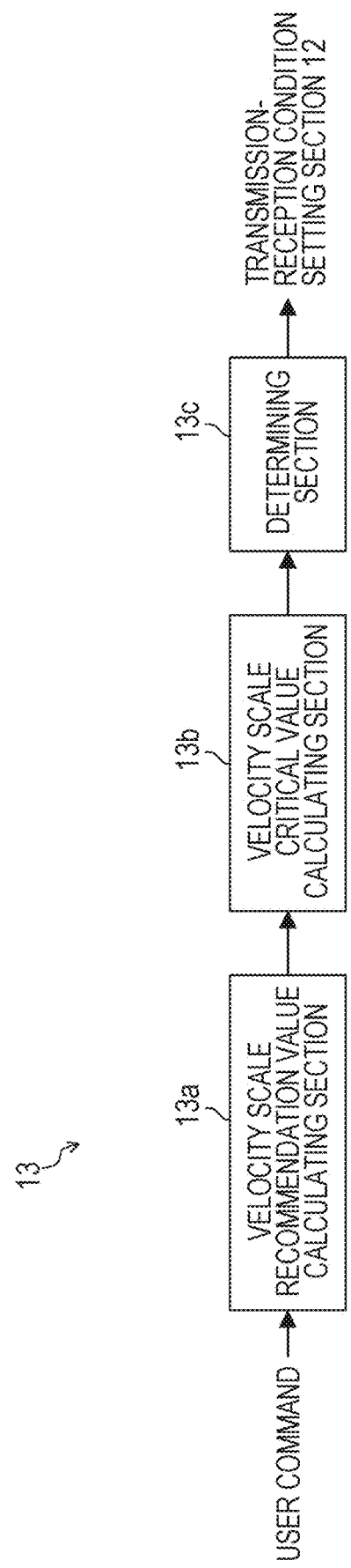
FIG. 7 is a diagram illustrating an example configuration of a velocity scale adjusting section according to the first embodiment.

FIG. 7 is a diagram illustrating an example configuration of velocity scale adjusting section 13 according to this embodiment.

Velocity scale adjusting section 13 includes velocity scale recommendation value calculating section 13a, velocity scale critical value calculating section 13b, and determining section 13c.

Velocity scale recommendation value calculating section 13a uses a technique similar to the technique described with reference to FIGS. 2A and 2B to calculate the recommendation value of the velocity scale (hereinafter referred to as "velocity scale recommendation value"). Velocity scale recommendation value calculating section 13a calculates the maximum value of the Doppler shift frequency during the observation target period with reference to the Doppler waveform during the immediately preceding observation target period and calculates the velocity scale recommendation value as expressed by expression (3) below on the basis of the maximum value and a velocity scale reference factor. The velocity scale reference factor is set to, for example, about 0.7.

$$Vsr = Vm \div \alpha \qquad \text{expression (3)}$$

(Here, Vsr represents the velocity scale recommendation value, α represents the velocity scale reference factor, and Vm represents the maximum value of the Doppler shift frequency during the observation target period.)

When calculating the velocity scale recommendation value, velocity scale recommendation value calculating section 13a may use the average value of the Doppler shift frequency during the observation target period instead of the maximum value of the Doppler shift frequency during the observation target period.

The "velocity scale recommendation value" is an optimum velocity scale in terms of, for example, resolution and visibility and is calculated on the basis of the maximum value or the average value of the Doppler shift frequency of the Doppler waveform during the immediately preceding observation target period. Therefore, as the velocity of the blood flow under measurement increases (for example, in a case where a jet backflow occurs in a cardiac blood vessel), the "velocity scale recommendation value" becomes a large value.

Figure 3:
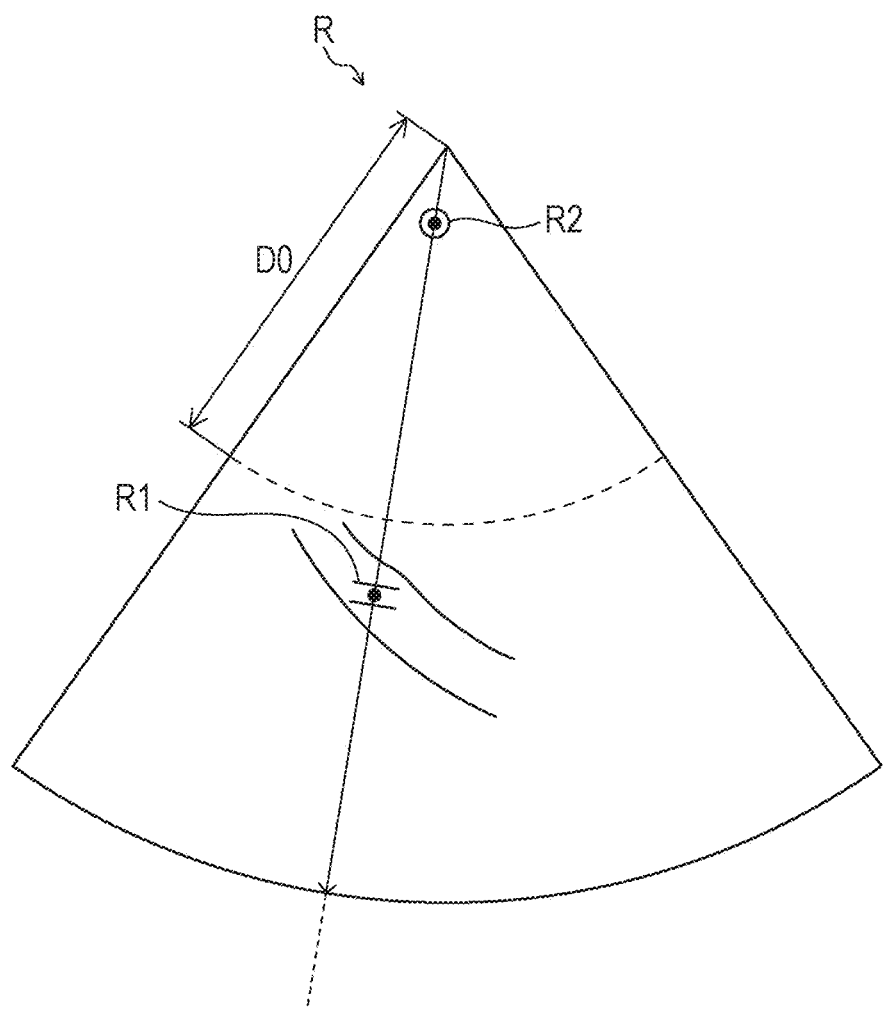
FIG. 3 is a diagram illustrating a measurement state in an HPRF measurement method.

Velocity scale critical value calculating section 13b calculates the critical value of the velocity scale (hereinafter referred to as "velocity scale critical value") at which the measurement state transitions from a non-HPRF state to the HPRF state on the basis of the sample gate position that is currently set (typically, the sample gate position set by the user). Here, as described with reference to FIG. 3, the "velocity scale critical value" means the critical point of the velocity scale (that is, the PRF) at which a transition from the non-HPRF state to the HPRF state occurs when the pulse-Doppler mode is performed, and is converted from the sample gate position. As the sample gate position becomes deeper, the time taken by the ultrasound to make a round trip over the distance from ultrasonic probe 200 to the sample gate position becomes longer, and therefore, the PRF for avoiding the HPRF state decreases (that is, the pulse repetition time increases). That is, as the sample gate position becomes deeper, the velocity scale critical value decreases.

Specifically, velocity scale critical value calculating section 13b calculates the critical frequency of the PRF that leads to the HPRF state, the critical frequency corresponding to the time taken by the ultrasound to make a round trip over the distance from ultrasonic probe 200 to the sample gate position. Velocity scale critical value calculating section 13b calculates the velocity scale critical value by using a known expression in the related art, such as expression (4) below.

$$Vc = c \times ft / (4 \times fs) \times 10^{-1} \qquad \text{expression (4)}$$

(Here, Vc [cm/s] represents the velocity scale critical value, c [m/s] represents the sonic velocity of the ultrasound in the subject, ft [kHz] represents the critical frequency of the PRF, and fs [MHz] represents the transmission (reference) frequency of the ultrasound beam.)

In expression (4), the transmission frequency of the ultrasound beam is the frequency of a burst wave that is transmitted as the ultrasound beam. In the pulse-Doppler mode, the Doppler shift frequency is calculated from the phase difference between the n-th transmission wave and the n+1-th transmission wave. Accordingly, as the transmission frequency of the ultrasound beam increases, the resolution of the Doppler shift frequency increases while the velocity scale critical value decreases.

Determining section 13c compares the velocity scale recommendation value with the velocity scale critical value and determines whether the velocity scale recommendation value is larger than the velocity scale critical value. In a case where the velocity scale recommendation value is equal to or smaller than the velocity scale critical value, determining section 13c sets the velocity scale recommendation value as a velocity scale to be used in measurement. In a case where the velocity scale recommendation value is larger than the velocity scale critical value, determining section 13c sets the velocity scale critical value as the velocity scale to be used in measurement.

That is, in the case where the velocity scale recommendation value is equal to or smaller than the velocity scale critical value, determining section 13c sets the velocity scale to the velocity scale recommendation value that is optimum in terms of, for example, resolution and visibility as in the related art. On the other hand, in the case where the velocity scale recommendation value is larger than the velocity scale critical value, determining section 13c sets the velocity scale critical value as the velocity scale to be used in measurement so as to avoid measurement in the HPRF state.

The velocity scale set by determining section 13c is referred to by transmission-reception condition setting section 12 to determine a condition for performing the pulse-Doppler mode.

In the case of setting the velocity scale to the velocity scale critical value, determining section 13c desirably notifies the user of the setting (that is, the velocity scale is currently set to the velocity scale critical value). Determining section 13c notifies the user of the setting by, for example, color reversal, text color change, blinking, or message display on the display screen of monitor 6.

Figure 8:
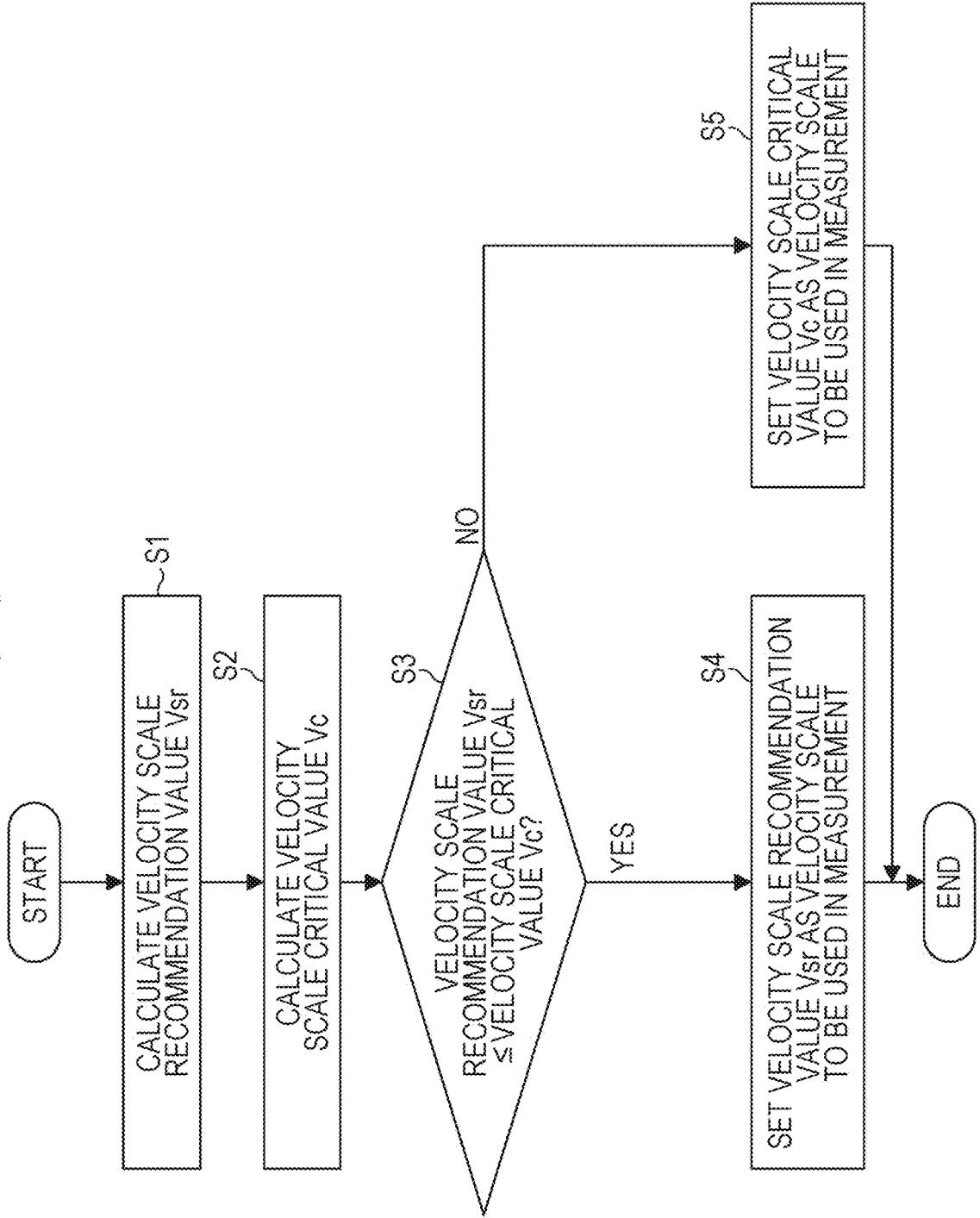
FIG. 8 is a flowchart illustrating an example operation of the velocity scale adjusting section according to the first embodiment.

FIG. 8 is a flowchart illustrating an example operation of velocity scale adjusting section 13 according to this embodiment. The flow in this flowchart starts in response to a velocity scale automatic adjustment command that is input by the user as a trigger.

Velocity scale adjusting section 13 first calculates velocity scale recommendation value Vsr (step S1). The method for calculating velocity scale recommendation value Vsr is as described with reference to expression (3) above.

Next, velocity scale adjusting section 13 calculates velocity scale critical value Vc (step S2). The method for calculating velocity scale critical value Vc is as described with reference to expression (4) above.

Next, velocity scale adjusting section 13 determines whether velocity scale recommendation value Vsr is equal to or smaller than velocity scale critical value Vc (step S3). In the case where velocity scale recommendation value Vsr is equal to or smaller than velocity scale critical value Vc (YES in step S3), velocity scale adjusting section 13 sets velocity scale recommendation value Vsr as the velocity scale to be used in measurement (step S4). On the other hand, in the case where velocity scale recommendation value Vsr is larger than velocity scale critical value Vc (NO in step S3), velocity scale adjusting section 13 sets velocity scale critical value Vc as the velocity scale to be used in measurement (step S5).

Here, the form in which velocity scale adjusting section 13 performs the velocity scale adjustment process in response to a velocity scale automatic adjustment command input by the user as a trigger has been described; however, velocity scale adjusting section 13 may perform the velocity scale adjustment process successively during measurement in the Doppler mode.

Effects

As described above, ultrasound diagnostic apparatus A (velocity scale adjusting section 13) according to this embodiment calculates the velocity scale recommendation value and the velocity scale critical value, compares these values with each other, and sets the velocity scale to be used in measurement. Accordingly, with ultrasound diagnostic apparatus A according to this embodiment, even in a case where the sample gate position is set to a deep position or the measurement target blood flow velocity is high, it is possible to automatically adjust the velocity scale while avoiding an unintended transition to the HPRF state.

First Modification to First Embodiment

It is desirable to configure ultrasound diagnostic apparatus A so as to be capable of measuring a high-velocity blood flow in the HPRF state as necessary.

For this, velocity scale adjusting section 13 is desirably capable of changing, in accordance with user setting, the method for setting the velocity scale in the case where the velocity scale recommendation value is larger than the velocity scale critical value. For example, in a case where the user performs setting so as to allow the velocity scale to exceed the velocity scale critical value, velocity scale adjusting section 13 may set the velocity scale recommendation value as the velocity scale to be used in measurement as is.

Second Modification to First Embodiment

Velocity scale adjusting section 13 may have a function of allowing setting of the velocity scale through a manual operation by the user in addition to the function of allowing automatic setting of the velocity scale. In this case, it is desirable to configure velocity scale adjusting section 13 so that the velocity scale to be used in measurement can be set to a value larger than the velocity scale critical value in the case of the manual operation by the user.

Accordingly, a skilled user can measure a high-velocity blood flow in the HPRF state as necessary.

Third Modification to First Embodiment

In a case where the velocity scale is set to a value larger than the velocity scale critical value at a time point before an automatic adjustment command for the velocity scale is given, it is desirable to configure velocity scale adjusting section 13 so that the upper limit of the velocity scale to be used in measurement is not limited to the velocity scale critical value.

Accordingly, a skilled user can measure a high-velocity blood flow in the HPRF state as necessary.

On the other hand, even in a case where the current velocity scale is set to a value larger than the velocity scale critical value through, for example, a manual operation by the user, when the velocity scale is automatically adjusted, the upper limit of the velocity scale to be used in measurement may be limited to the velocity scale critical value.

Second Embodiment

Figure 9:
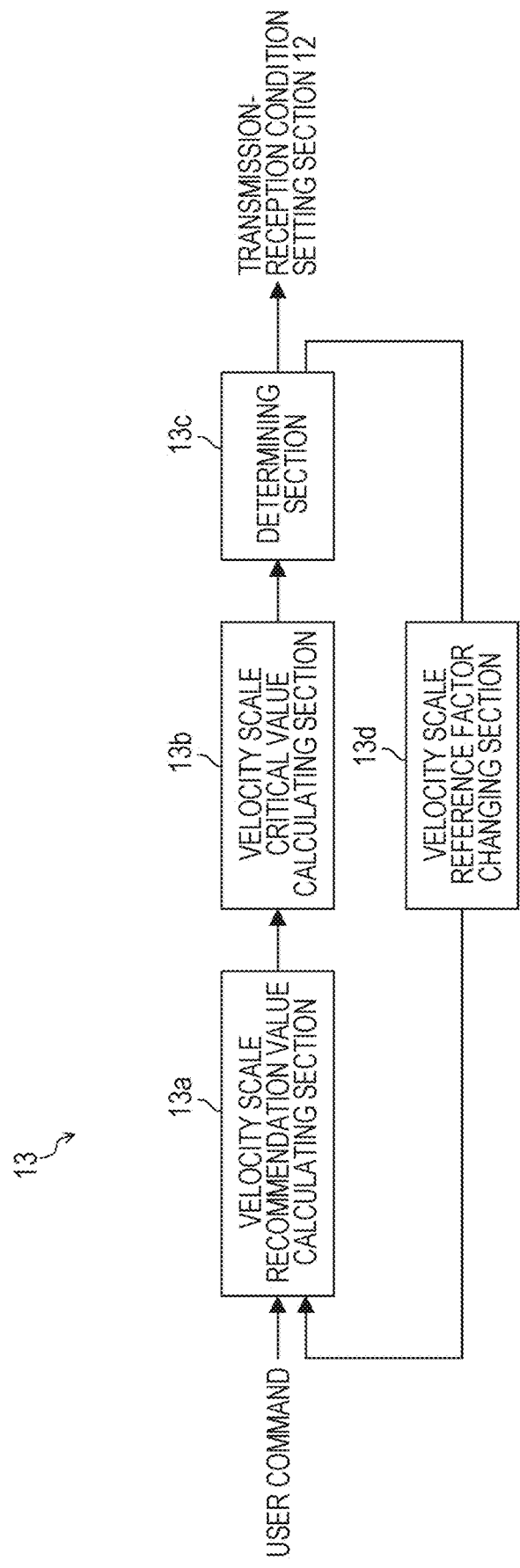
FIG. 9 is a diagram illustrating an example configuration of the velocity scale adjusting section according to a second embodiment.

FIG. 9 is a diagram illustrating an example configuration of velocity scale adjusting section 13 according to a second embodiment.

Ultrasound diagnostic apparatus A according to this embodiment is different from that in the first embodiment in that velocity scale adjusting section 13 includes velocity scale reference factor changing section 13d. A description of an element common to the first embodiment is omitted (hereinafter, the same applies to the other embodiments).

Velocity scale reference factor changing section 13d obtains the result of comparing the velocity scale recommendation value with the velocity scale critical value from determining section 13c. In the case where the velocity scale recommendation value becomes larger than the velocity scale critical value, velocity scale reference factor changing section 13d changes the velocity scale reference factor to a value larger than an initial setting and causes velocity scale recommendation value calculating section 13a to calculate again the velocity scale recommendation value.

The velocity scale reference factor is set to, for example a value larger than 50% and smaller than 100% at the start of diagnosis, and thereafter, changed to 100% in a case where the velocity scale recommendation value calculated on the basis of the velocity scale reference factor corresponding to the initial setting becomes larger than the velocity scale critical value.

Figure 2B:
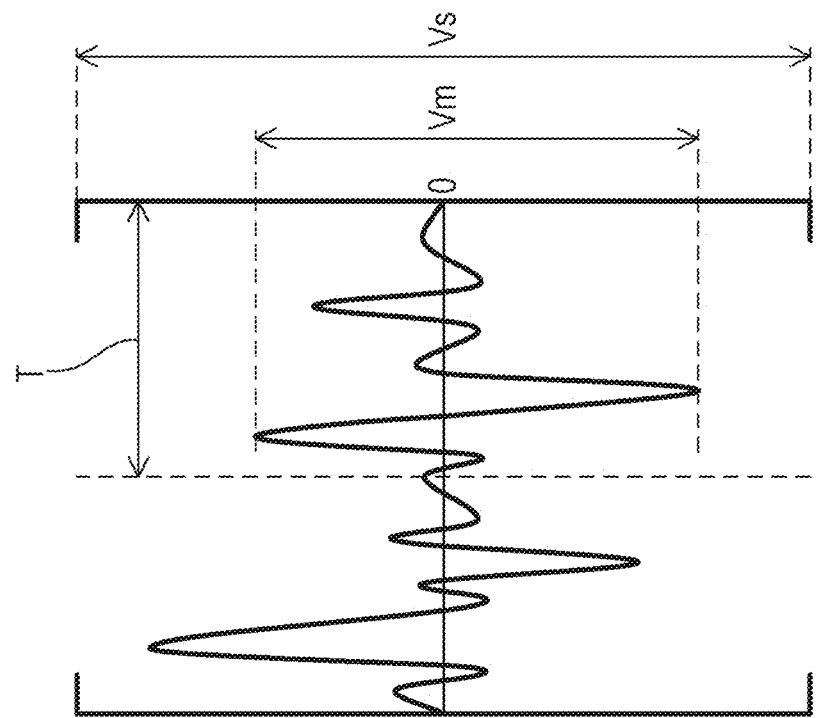
FIGS. 2A and 2B are diagrams for describing a function of automatically adjusting the velocity scale of an ultrasound diagnostic apparatus according to the related art.
Figure 2A:
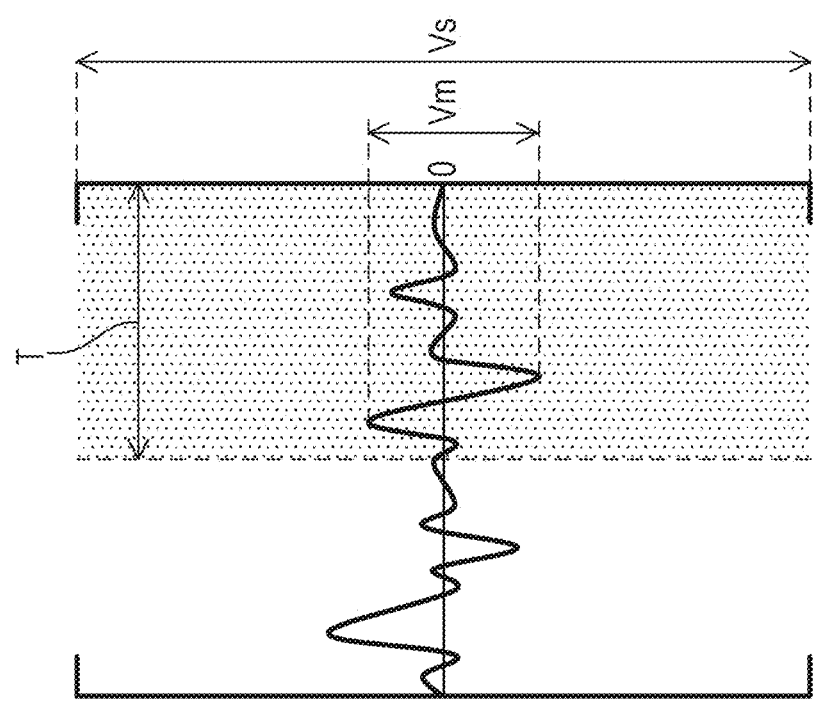

The velocity scale reference factor is a reference value that determines the magnitude of the velocity scale relative to the maximum value of the Doppler shift frequency during the observation target period and is set to a reference value with which the velocity scale becomes optimum in terms of, for example, resolution and visibility at the start of diagnosis (for example, in FIG. 2B, Maximum value Vm of Doppler shift frequency during observation target period/Velocity scale Vs=0.7). Therefore, in a case of taking into consideration only keeping the maximum value of the Doppler shift frequency during the observation target period within the range of the velocity scale, the velocity scale can be set to a value smaller than the current setting.

From this viewpoint, velocity scale reference factor changing section 13d increases the velocity scale reference factor to thereby decrease the velocity scale recommendation value. When the velocity scale recommendation value is decreased, the velocity scale recommendation value can be changed to a value equal to or smaller than the velocity scale critical value. In other words, velocity scale adjusting section 13 lowers the velocity scale recommendation value to a value approximately equal to the maximum value of the Doppler shift frequency during the current observation target period. Accordingly, even in a case where the velocity scale recommendation value is set as the velocity scale to be used in measurement, it is possible to continue the pulse-Doppler-mode operation without a transition to the HPRF state.

In a case where the maximum value of the Doppler shift frequency during the observation target period becomes smaller than the velocity scale critical value after changing the velocity scale reference factor to a value (for example, 100%) for avoiding the HPRF state, velocity scale reference factor changing section 13d may reset the velocity scale reference factor to the value set at the start of diagnosis.

Figure 10:
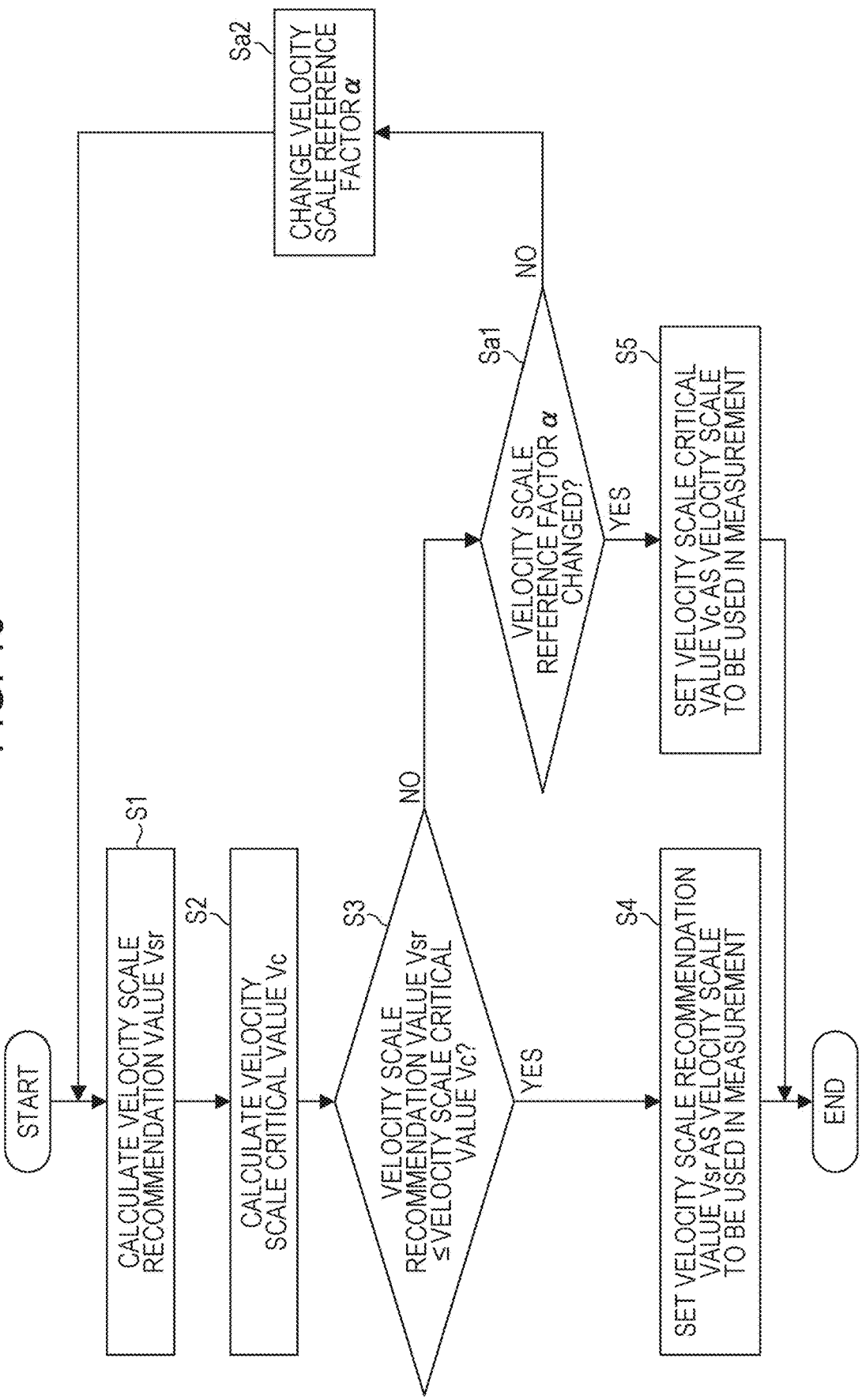
FIG. 10 is a flowchart illustrating an example operation of the velocity scale adjusting section according to the second embodiment.

FIG. 10 is a flowchart illustrating an example operation of velocity scale adjusting section 13 according to this embodiment. The flowchart in FIG. 10 is different from the flowchart in FIG. 8 in that step Sa1 and step Sa2 are added.

In the case where the velocity scale recommendation value becomes larger than the velocity scale critical value (NO in step S3), velocity scale adjusting section 13 determines in step Sa1 whether the velocity scale reference factor is already changed. In a case where the velocity scale reference factor is already changed (YES in step Sa1), the flow proceeds to step S5. On the other hand, in a case where the velocity scale reference factor is not yet changed (NO in step Sa1), the flow proceeds to step Sa2.

In step Sa2, velocity scale adjusting section 13 changes the velocity scale reference factor to a predetermined value (for example, 100%) for avoiding the HPRF state from the value (for example, 70%) set at the start of diagnosis (that is, increases the velocity scale reference factor). Subsequently, the flow returns to step S1, and velocity scale adjusting section 13 again calculates the velocity scale recommendation value.

As described above, with ultrasound diagnostic apparatus A according to this embodiment, it is possible to suppress a transition to the HPRF state when the velocity scale is automatically adjusted.

Third Embodiment

Figure 11:
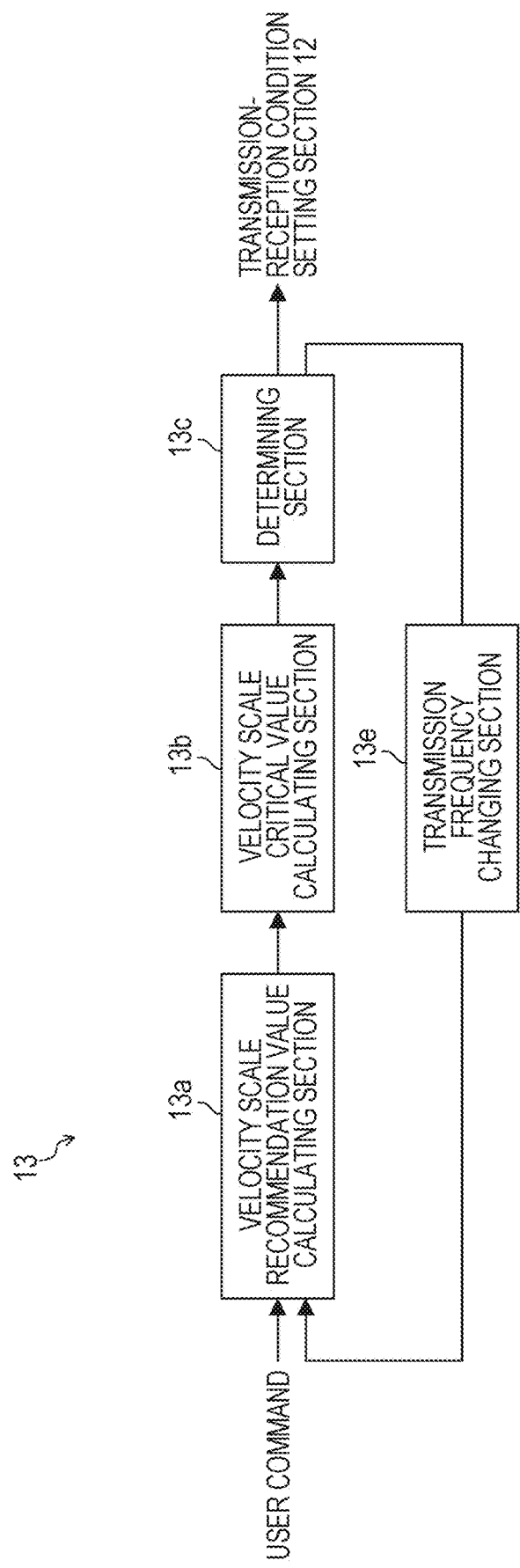
FIG. 11 is a diagram illustrating an example configuration of the velocity scale adjusting section according to a third embodiment.

FIG. 11 is a diagram illustrating an example configuration of velocity scale adjusting section 13 according to a third embodiment.

Ultrasound diagnostic apparatus A according to this embodiment is different from that in the first embodiment in that velocity scale adjusting section 13 includes transmission frequency changing section 13e.

Transmission frequency changing section 13e obtains the result of comparing the velocity scale recommendation value with the velocity scale critical value from determining section 13c. In the case where the velocity scale recommendation value becomes larger than the velocity scale critical value, transmission frequency changing section 13e lowers the transmission frequency of the ultrasound beam and causes velocity scale recommendation value calculating section 13a to calculate again the velocity scale recommendation value.

The transmission frequency of the ultrasound beam is usually set to a relatively high frequency (for example, 10 MHz) for increasing resolution with which the Doppler shift frequency is detected.

As described with reference to expression (4) above, the velocity scale critical value depends on the transmission frequency of the ultrasound beam and can be increased by lowering the transmission frequency of the ultrasound beam. When the velocity scale critical value is increased, it is possible to continue the pulse-Doppler-mode operation in the state where the velocity scale recommendation value is equal to or smaller than the velocity scale critical value. That is, it is possible to continue the pulse-Doppler-mode operation without a transition to the HPRF state.

From this viewpoint, in the case where the velocity scale recommendation value becomes larger than the velocity scale critical value, transmission frequency changing section 13e changes the transmission frequency of the ultrasound beam from an initially set frequency (for example, 2.5 MHz)

that is set at the start of diagnosis to a predetermined frequency (for example, 2.0 MHz) for avoiding the HPRF state (that is, decreases the transmission frequency).

In a case where the maximum value of the Doppler shift frequency during the observation target period becomes smaller than the velocity scale critical value after changing the transmission frequency of the ultrasound beam to the frequency for avoiding the HPRF state, transmission frequency changing section 13e may reset the transmission frequency of the ultrasound beam to the frequency set at the start of diagnosis.

As described above, with ultrasound diagnostic apparatus A according to this embodiment, it is possible to suppress a transition to the HPRF state when the velocity scale is automatically adjusted.

Fourth Embodiment

Figures 12, 13:
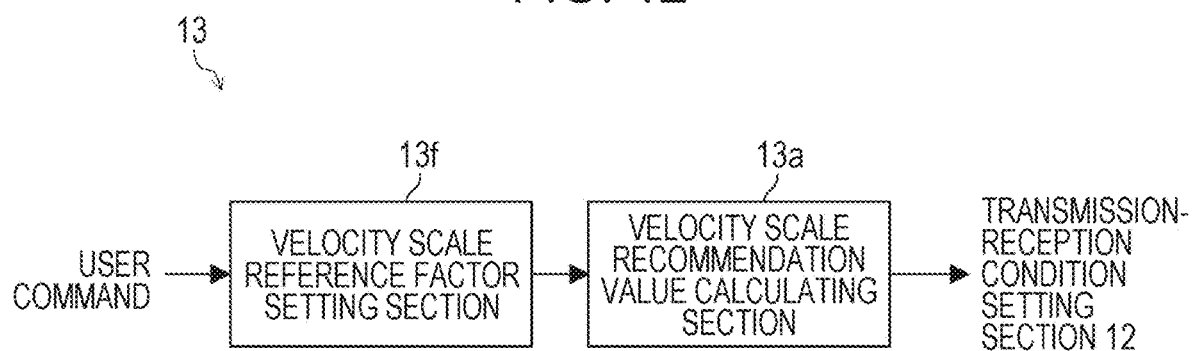
FIG. 12 is a diagram illustrating an example configuration of the velocity scale adjusting section according to a fourth embodiment.
FIG. 13 is a diagram illustrating example table data according to the fourth embodiment in which diagnostic conditions and settings of a velocity scale reference factor are associated with each other.

FIG. 12 is a diagram illustrating an example configuration of velocity scale adjusting section 13 according to a fourth embodiment.

Ultrasound diagnostic apparatus A according to this embodiment is different from that in the first embodiment in that velocity scale adjusting section 13 is constituted by velocity scale reference factor setting section 13f and velocity scale recommendation value calculating section 13a.

At the start of diagnosis, velocity scale reference factor setting section 13f sets the velocity scale reference factor on the basis of a diagnostic condition set by the user. Velocity scale recommendation value calculating section 13a calculates the velocity scale recommendation value by using expression (3) above with reference to the velocity scale reference factor set by velocity scale reference factor setting section 13f. In this embodiment, the velocity scale recommendation value calculated by velocity scale recommendation value calculating section 13a is set as the velocity scale to be used in measurement as is.

The velocity scale reference factor is usually set to a reference value with which the velocity scale becomes optimum in terms of, for example, resolution and visibility of the Doppler waveform. However, depending on the diagnosis target area, the blood flow velocity temporally changes to a large degree. Therefore, it may be desirable to set the velocity scale at the start of diagnosis so as to suppress a transition to the HPRF state.

From this viewpoint, velocity scale reference factor setting section 13f retains in advance table data in which diagnostic conditions and settings of the velocity scale reference factor are associated with each other. Velocity scale reference factor setting section 13f refers to the table data and sets the velocity scale reference factor on the basis of the diagnostic condition set by the user.

FIG. 13 is a diagram illustrating example table data in which diagnostic conditions and settings of the velocity scale reference factor are associated with each other. The table data specifies that, for example, the velocity scale reference factor is set to 0.95 in a case where the diagnosis target area is the heart and that the velocity scale reference factor is set to 0.70 in a case where the diagnosis target area is other than the heart.

As the diagnostic condition to be referred to for determining the velocity scale reference factor, only the diagnosis target area is covered here; however, the diagnostic condition may further include, for example, information regarding the age or sex of the subject and information regarding the type of ultrasonic probe 200.

The diagnostic condition may further include information in which either a Doppler mode for detecting a blood flow or a Doppler mode for detecting motion of tissue is specified.

As described above, with ultrasound diagnostic apparatus A according to this embodiment, it is possible to suppress a transition to the HPRF state when the velocity scale is automatically adjusted.

Other Embodiments

The present invention is not limited to the above-described embodiments, and various modified forms are possible.

In the above-described embodiments, various example configurations of ultrasound diagnostic apparatus A have been illustrated. However, any of the forms illustrated in the respective embodiments may be combined and used as a matter of course.

For example, velocity scale adjusting section 13 may include all of velocity scale recommendation value calculating section 13a, velocity scale critical value calculating section 13b, determining section 13c, velocity scale reference factor changing section 13d, transmission frequency changing section 13e, and velocity scale reference factor setting section 13f. Alternatively, velocity scale adjusting section 13 may cause at least one of velocity scale reference factor changing section 13d, transmission frequency changing section 13e, and velocity scale reference factor setting section 13f to function on the basis of user setting.

In the above-described embodiments, tomographic image generating section 3, Doppler processing section 4, and display processing section 5 may be implemented as, for example, a digital arithmetic circuit constituted by an application-specific integrated circuit (ASIC), a field-programmable gate array (FPGA), or the like. Some or all of the sections may be implemented by, for example, a digital signal processor (DSP), a central processing unit (CPU), or general-purpose graphics processing units (GPGPUs) performing arithmetic processing in accordance with a program.

In the above-described embodiments, control device 10 may be constituted by, for example, a CPU, a read-only memory (ROM), a random access memory (RAM), and so on, and the functions of control device 10 may be implemented by the CPU referring to a control program and various types of data stored in the ROM or the RAM. Some or all of the functions of control device 10 may be implemented as a DSP or a dedicated hardware circuit.

Although embodiments of the present invention have been described and illustrated in detail, the disclosed embodiments are made for purpose of illustration and example only and not limitation. The scope of the present invention should be interpreted by terms of the appended claims.

With the ultrasound diagnostic apparatus according to the present disclosure, it is possible to automatically adjust the velocity scale to be used in generation of the Doppler waveform while avoiding an unintended transition to the HPRF state.

What is claimed is:
1. An ultrasound diagnostic apparatus comprising:
a transmitter that repeatedly transmits an ultrasound beam from an ultrasonic probe into a subject at a predetermined pulse repetition frequency;

a receiver that receives via the ultrasonic probe a reflected wave resulting from the ultrasound beam reflected in the subject;

a Doppler processor that detects a Doppler shift frequency resulting from a blood flow or motion of tissue in the subject, based on a reception signal corresponding to the reflected wave from a sample gate position in the subject; and a velocity scale adjuster that adjusts a velocity scale determining the pulse repetition frequency, based on a Doppler waveform corresponding to the Doppler shift frequency during an observation target period, wherein the pulse repetition frequency at which the transmitter repeatedly transmits the ultrasound beam is determined according to the velocity scale adjusted by the velocity scale adjuster, wherein:

the velocity scale adjuster sets a factor that determines a magnitude of the velocity scale with respect to a maximum value of the Doppler shift frequency during the observation target period, based on a diagnostic condition set by a user, and the velocity scale adjuster further sets the velocity scale to be used in measurement, based on the factor and the Doppler waveform, the velocity scale determines a displayable velocity range of the Doppler waveform along a vertical axis representing the Doppler shift frequency, the factor determines how large the Doppler waveform appears along the vertical axis in the adjusted velocity scale, the velocity scale adjuster calculates a velocity scale recommendation value according to an expression $$V_{sr}=V_m \div \alpha$$

where Vsr represents the velocity scale recommendation value, Vm represents the maximum value of the Doppler shift frequency during the observation target period, and α represents the factor, the velocity scale adjuster sets the calculated velocity scale recommendation value as the velocity scale, and the velocity scale adjuster sets the factor by referring to table data stored in advance in which a plurality of diagnostic conditions and a plurality of values for the factor are respectively associated with each other, and selecting, from among the plurality of values for the factor, a value for the factor that is associated with a diagnostic condition, from among the plurality of diagnostic conditions, which corresponds to the diagnostic condition set by the user.

2. The ultrasound diagnostic apparatus according to claim 1, wherein the diagnostic condition includes information regarding a diagnosis target area in the subject.

3. The ultrasound diagnostic apparatus according to claim 1, wherein the diagnostic condition includes information regarding an age or a sex of the subject.

4. The ultrasound diagnostic apparatus according to claim 1, wherein the diagnostic condition includes information regarding a type of the ultrasonic probe.

5. The ultrasound diagnostic apparatus according to claim 1, wherein the diagnostic condition includes information in which either a Doppler mode for detecting a blood flow or a Doppler mode for detecting motion of tissue is specified.

* * * * *